United States Patent [19]

Karasawa et al.

[11] Patent Number: 5,196,928
[45] Date of Patent: Mar. 23, 1993

[54] ENDOSCOPE SYSTEM FOR SIMULTANEOUSLY DISPLAYING TWO ENDOSCOPIC IMAGES ON A SHARED MONITOR

[75] Inventors: Isamu Karasawa; Yasuyuki Kaneko; Masahiko Hamano, all of Hachioji; Kazufumi Takamizawa, Chofu; Matsumi Oshima; Hideyuki Shoji, both of Hachioji; Ken-ya Inomata, Mitaka; Atsushi Amano, Hachioji; Toshiaki Nishikori, Sagamihara; Akira Osawa, Yokohama, all of Japan

[73] Assignee: Olympus Optical Co., Ltd., Tokyo, Japan

[21] Appl. No.: 828,744

[22] Filed: Jan. 31, 1992

[30] Foreign Application Priority Data

Apr. 2, 1991 [JP] Japan ................ 3-070159

[51] Int. Cl.[5] .................. A61B 1/04; A61B 1/06; H04N 5/272
[52] U.S. Cl. ........................ 358/98; 128/6; 358/183
[58] Field of Search ............ 358/98, 183; 128/6

[56] References Cited

U.S. PATENT DOCUMENTS

| 4,712,133 | 12/1987 | Kikuchi | 358/98 |
| 4,920,413 | 4/1990 | Nakamura et al. | 358/98 |
| 4,993,404 | 2/1991 | Lane | 128/4 |
| 4,998,972 | 3/1991 | Chin | 358/98 |

Primary Examiner—Howard W. Britton
Attorney, Agent, or Firm—Armstrong, Westerman, Hattori, McLeland & Naughton

[57] ABSTRACT

An endoscope system comprises first and second endoscopes each of which includes an elongated insertion tube and an imaging device, a light source for supplying illumination light to the endoscopes, a function for processing a signal originating from one of the imaging devices, and a video processor which mixes the signal with at least a signal sent from an external input terminal and outputs a given video signal corresponding to the first and second endoscopic images. The video signal provided by the video processor is output to a shared monitor, thus displaying two endoscopic images simultaneously.

20 Claims, 16 Drawing Sheets

FIG. 4
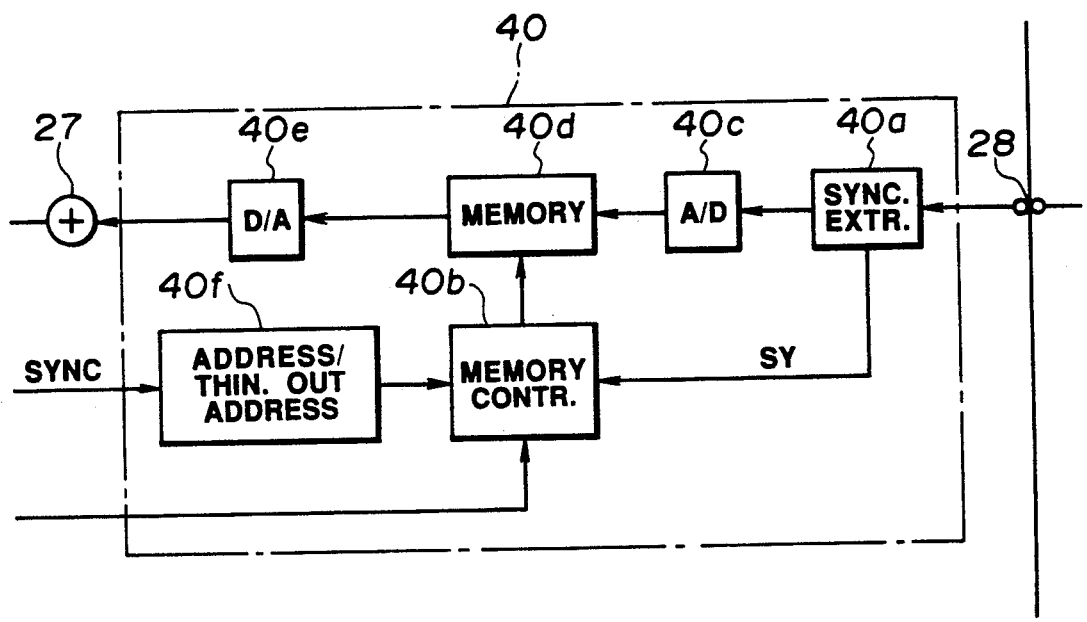
FIG. 7a FIG. 7b FIG. 7c
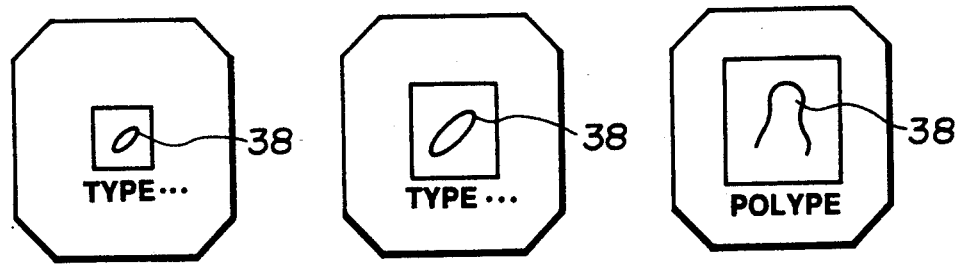

FIG. 9
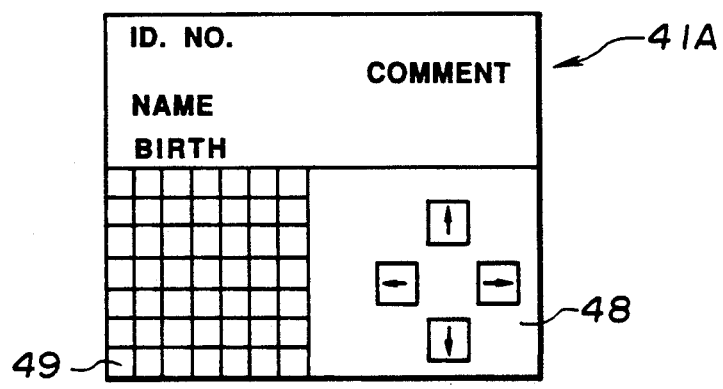
FIG. 10a    FIG. 10b
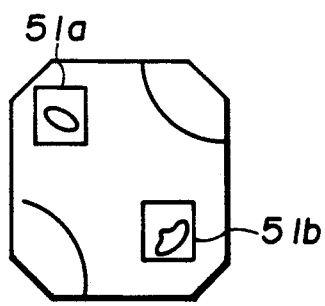    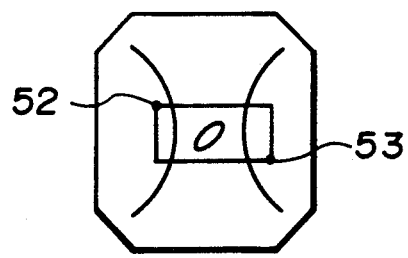

ENDOSCOPE SYSTEM FOR SIMULTANEOUSLY DISPLAYING TWO ENDOSCOPIC IMAGES ON A SHARED MONITOR

BACKGROUND OF THE INVENTION

1. Field of the Invention

The present invention relates to an endoscope system for simultaneously displaying endoscopic images produced by two endoscopes on the same monitor.

2. Description of the Related Art

Parent and child scopes are sometimes employed as a unit or system for endoscopic observation of the bile duct or other small duct in a body cavity. This kind of system comprises a parent scope which has channel whose internal diameter is large enough for a child scope to run through, a child scope which is routed through the channel, a light source for supplying illumination light to the scopes for easy observation, video processors for processing video signals originating from the imaging means of the scopes, and monitors for displaying the images.

To display a parent scope image produced by a parent scope on a monitor, an electric signal originating from a charge coupled device (CCD) at the distal end of an endoscope must be converted into a video signal using a video processor. As for a child scope inserted into the channel of the parent scope, the CCD in the TV camera head mounted on the eyepiece section of the child scope forms a child scope image. Then, the electric signal resulting from the child scope image is converted into a video signal by other video processor corresponding to the child scope, then displayed on other monitor corresponding to the child scope.

For observation using parent scopes, electronic endoscope systems are needed for each of the parent scopes. This results in an increase in the space occupied by the endoscope systems within an endoscope room. The installation site for monitors, in particular, is restricted. That is to say, monitors must be installed in a place where operators can view them easily. However, a space wide enough to install two monitors is sometimes unavailable.

U.S. Pat. No. 4,920,413 has disclosed a system in which an X-ray image obtained in vitro and an angioscopic image obtained in vivo can be displayed on a shared monitor. The X-ray image is a fluoroscopic image obtained in vitro, which cannot be used to route an endoscope into a complicated region in a body. In addition, an object to be observed cannot be observed directly. Therefore, this system is unsuitable for detailed observation or treatment of an object.

SUMMARY OF THE INVENTION

The principal object of the present invention is to provide an endoscope system permitting observation of images produced by parent and child scopes in a limited space.

Another object of the invention is to provide an endoscope system which can be designed compactly to improve accessibility to a complicated region or facilitate efficiency in observation or treatment.

The present invention includes a first endoscope for producing a first endoscopic image, a second endoscope for producing a second endoscopic image, an external input terminal, a video processor capable of inputting the second endoscopic image, and a shared monitor for displaying video signals processed by the video processor. The first endoscopic image and second endoscopic image can be displayed on the shared monitor simultaneously. This allows the endoscope system to be used in a limited installation site.

BRIEF DESCRIPTION OF THE DRAWINGS

FIGS. 1 to 7 relate to the first embodiment of the present invention;

FIG. 1 is an oblique view of the overall configuration of the first embodiment;

FIG. 2 is a block diagram showing the configuration of a parent scope system;

FIG. 3 is an explanatory diagram showing examples of displaying images on a monitor;

FIG. 4 is a block diagram showing the configuration of a superimpose processing circuit;

FIG. 5 is a block diagram showing the configuration of a child scope system;

FIGS. 6 and 7 are explanatory diagrams showing examples of displaying images on a monitor with only a parent scope connected;

FIG. 9 is an explanatory diagram showing a keyboard operation screen for the system shown in FIG. 8;

FIG. 10 is an explanatory diagram showing that a plurality of indication frames are displayed on a monitor;

DESCRIPTION OF THE PREFERRED EMBODIMENTS

The present invention will be described specifically in conjunction with the drawings below.

Figure 1:
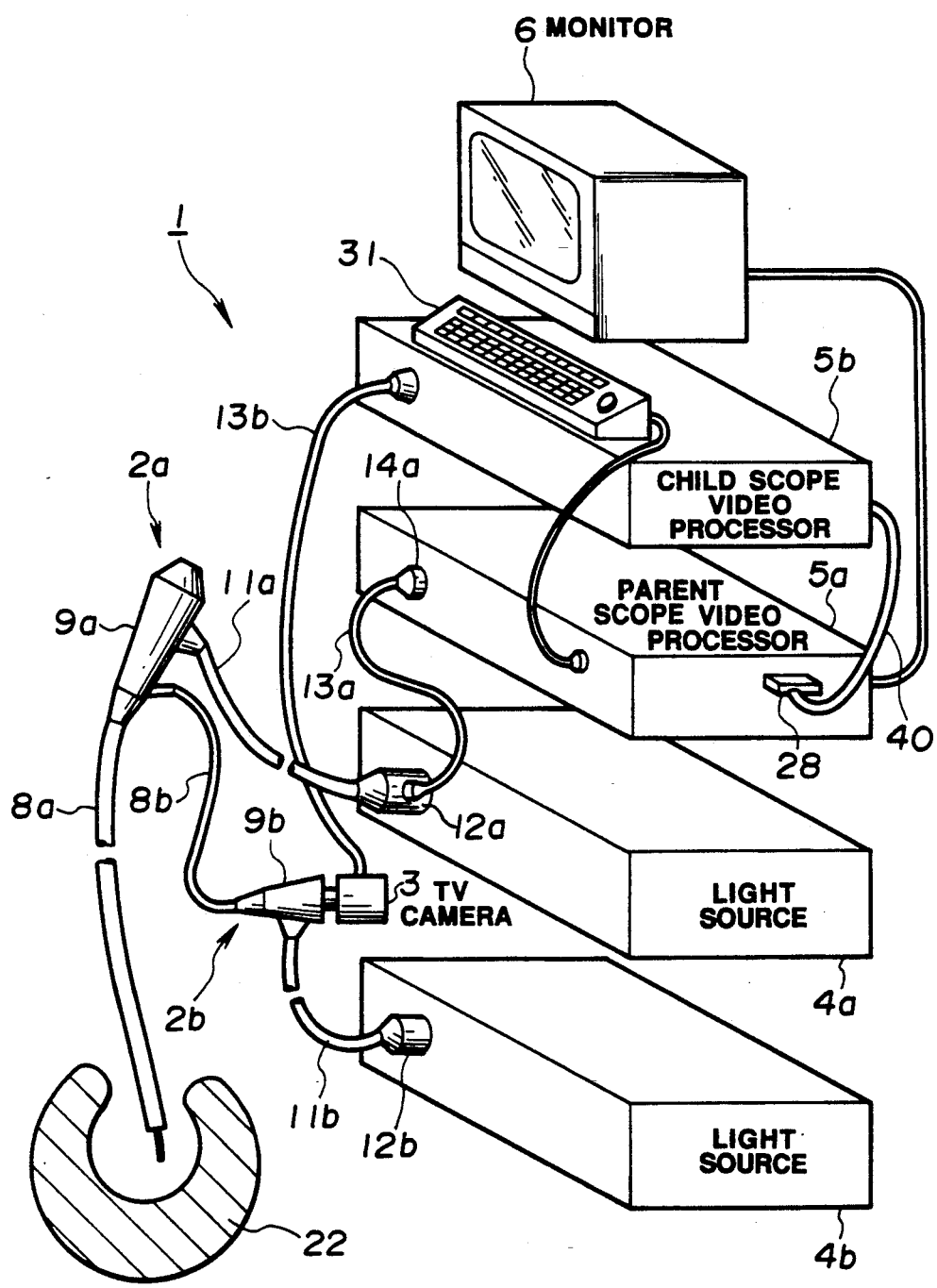

As shown in FIG. 1, an electronic endoscope system 1 according to the first embodiment comprises an electronic scope 2a or a parent scope, a fiberscope 2b or a child scope to be inserted into the channel of the electronic scope 2a, a TV camera 3 mounted on the fiberscope 2b (the fiberscope 2b on which the TV camera 3 is mounted is referred to as an external TV camera scope), a first light source 4a and a second light source 4b for supplying illumination light to the scopes 2a and 2b, parent scope and child scope video processors 5a 5b, and a monitor 6 connected to the parent scope video processor 5a.

Figure 2:
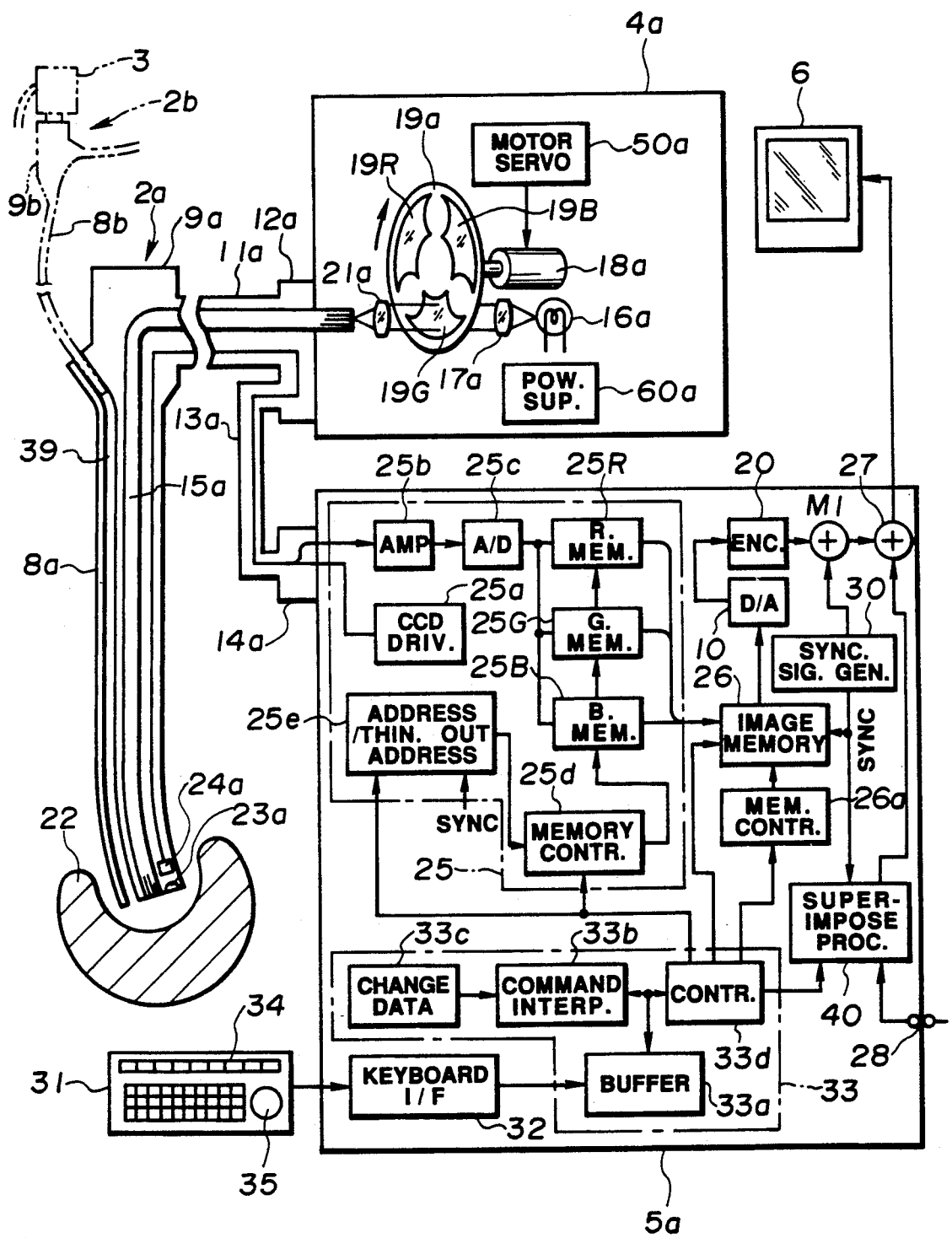

FIG. 2 shows a specific configuration of an electronic endoscope system for the parent scope. In FIG. 2, the electronic scope 2a has an elongated insertion tube 8a. An operating section 9a is formed at the back of the insertion tube 8a. A universal cable 11a therefor extends from the side of the operating section 9a. A connector 12a attached to the end of the cable 11a can be connected to the light source 4a. A signal cable 13a is extending from the side of the connector 12a. A connector 14a attached to the end of the signal cable 13a can be connected to the parent scope video processor 5a.

A light guide 15a therefor runs through the insertion tube 8a. When the connector 12a is connected to the light source 4a, white illumination light from a lamp 16a is converged in parallel by a lens 17a and changed to be field-sequential light of R, G, and B components by a rotary filter 19a which is driven by a motor 18a to rotate.

Specifically, the rotary filter 19a is provided with fan-shaped color filters 19R, 19G, and 19B in the circumferential direction to transmit light having the wavelengths of R, G, and B components. The color transmission filters 19R, 19G, and 19B are alternately positioned on an optical path to produce R, G, and B field-sequential beams. The R, G, and B field-sequential beams are converged by a lens 21a and supplied to the light guide 15a. The motor 18a is controlled by a motor servo circuit 50a so that the rotating speed will be constant (for example, 1800 rpm).

The lamp 16a is provided with light emission power by a power supply 60a.

Light transmitted by the light guide 15a is emitted forward from the end surface at the distal end to illuminate, for example, a lesion in a living body 22. The image of the lesion or other subject illuminated is formed on a CCD 24a installed on the focal plane by an objective lens 23a mounted at the distal end, then photoelectrically transferred by the CCD 24a.

The CCD 24 is provided with a drive signal sent from a drive circuit 25a in an image processing unit 25 of a video processor 5a. Thereby, a photoelectrically-transferred image signal is read and input into an amplifier 25b in the image processing unit 25. After being amplified by the amplifier 25b, the signal is converted into a digital signal by an A/D converter 25c. After that, the digital signal is written sequentially in R, G, and B memories 25R, 25G, and 25B respectively by a memory controller 25d.

Image data written sequentially in the R, G, and B memories 25R, 25G, and 25B is read simultaneously by the memory controller 25d, then written in an image memory 26. When the memory controller 25d reads image data from the R, G, and B memories 25R, 25G, and 25B, it accesses ordinary addresses or thinned-out addresses generated by an address/thinned-out address generation circuit therefor 25e. The address/thinned-out address generation circuit 25e can selectively generate addresses for normal-size display or those for reduced-size display; such as, thinned-out addresses. Thinned-out addresses are picked up from normal addresses by a counter or frequency divider.

The address/thinned-out address generation circuit 25e generates addresses or thinned-out addresses according to the timing controlled with a synchronizing signal SYNC sent from a synchronizing signal generation circuit 20.

In response to a control signal for display change sent from a CPU 33, the address/thinned-out address generation circuit 25e outputs thinned-out addresses to the memory controller 25d. Then, the R, G, and B memories 25R, 25G, and 25B output reduced image data. The reduced image data is controlled by a memory controller 26a so that it will be stored in an area of an image memory 26 differing from the one for non-reduced image data.

Writing in and reading from the image memory 26 are controlled by the memory controller 26a. The image memory 26 has a data storage capacity for one plane (R, G, and B plane) displayed in color on a screen of the monitor 6. Patient data entered at a keyboard 31 can be written in the image memory 26.

Input data entered by operating keys on the keyboard 31 is stored temporarily in a buffer memory 33a in the CPU 33 via a keyboard interface 32. The input data temporarily stored in the buffer memory 33a is interpreted (translated) by a command interpreter 33b. The command interpreter 33b compares input data with switching data in, for example, a switching data memory 33c, thus determining whether the input data is command data specifying a specific operation, or, in this case, a switching command (data) for switching two images.

The result of the determination by the command interpreter 33b is transferred to a controller 33d. If the input data is found to be patient data, the controller 33d transfers the patient data into the image memory 26. If the input data is a switching command, the controller 33 outputs a display control signal for changing the display state or switching images produced by the electronic scope 2a and TV camera to the image processing unit 25 and superimpose processing circuit 30.

R, G, and B image data and patient data read from the image memory 26 are converted into analog signals by a D/A converter 10, then converted into, for example, NTSC video signal components by an encoder 20. Then, the NTSC video signal components are mixed with a synchronizing signal SYNC originating from the synchronizing signal generator 30 by a first mixer M1 to generate an NTSC composite video signal. Then, the NTSC composite video signal is input into a second mixer 27.

Video signal components originating from the superimpose processing circuit 40 are also input to and mixed by the second mixer 27. As a result, an NTSC composite video signal containing data of two images is output to the monitor 6.

A video signal sent from an external unit via an external input terminal 28; that is, a video signal sent from a child scope video processor 5b is input into the superimpose processing circuit 40.

When provided with a video signal originating from a child scope via the external input terminal 28, the mixer 27 mixes it with a video signal (including patient data) sent from the image memory 26, then outputs the mixed signal to the monitor 6. Thus, as shown in FIG. 4b or 4c, endoscopic images 29a and 29b are displayed simultaneously.

Figure 3A:
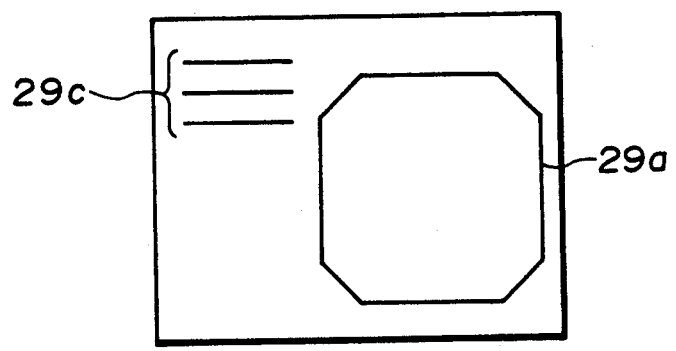
Figure 3B:
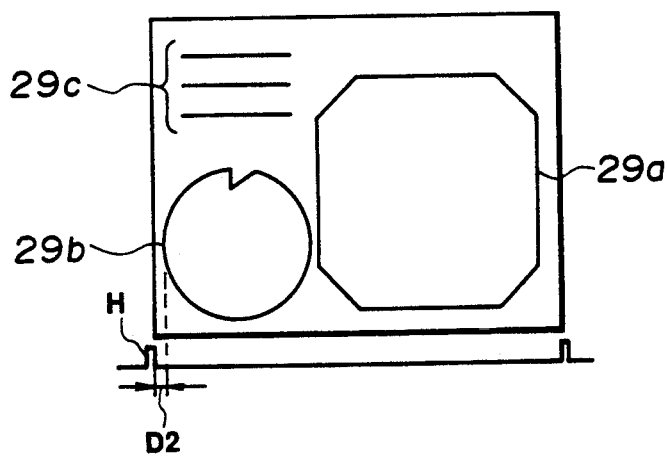

The endoscope image 29a originates from the electronic scope 2a, and the other endoscopic image 28b, a child scope. Therefore, when only the electronic endoscope 2a is employed, the image 29a alone is displayed as shown in FIG. 3a. Patient data 29c is displayed on the left of the image 29a (above the image 29a in FIG. 3c). A normal display state is shown in FIG. 3b. When a switching command is entered at the keyboard 31, the parent scope image 29a and child scope image 29b may be switched and enlarged for observation if an operator wishes so. For switching images in this way, the superimpose processing circuit 40 having a configuration, for example, shown in FIG. 4 is installed.

A video signal provided via the external input terminal 28 is input to a synchronizing signal extraction circuit 40a. Then a synchronizing signal SY is extracted from the video signal. The extracted synchronizing signal SY is input to a memory controller 40b.

Video signal components left after the synchronizing signal SY is removed are converted into a digital signal by an A/D converter 40c, then written in a memory 40d. Writing in and reading from the memory 40d are controlled by a memory controller 40b. The memory controller 40b writes image data in the memory 40d in synchronization with the synchronizing signal SY extracted by the synchronizing signal extraction circuit 40a.

Image data read from the memory 40d is converted into an analog video signal by a D/A converter 40e, input into the mixer 27, mixed with a video signal sent from the image memory 26, then output to the monitor 6.

When reading image data from the memory 40d, the memory controller 40c accesses normal addresses or thinned-out addresses provided by an address/thinned-out address generation circuit 40f. The address/thinned-out address generation circuit 40f generates addresses or thinned-out addresses according to the timing controlled with a synchronizing signal SYNC sent from the synchronizing signal generation circuit 30. Thus, the timing for reading image data from the memory 40a synchronizes with that for reading image data from the image memory 26.

In response to a control signal for display change sent from the controller 33d of the CPU 33, the address/thinned-out address generation circuit 40f outputs thinned-out addresses to the memory controller 40e. Then, the memory 40d output reduced image data. For thinned-out addresses, the memory controller 40e controls an internal delay circuit (not shown) to vary the delay and provides the reduced image data to the memory 40d. Thus, the reduced image data will be output from the memory 40d according to the timing different from that for non-reduced data.

Figure 3C:
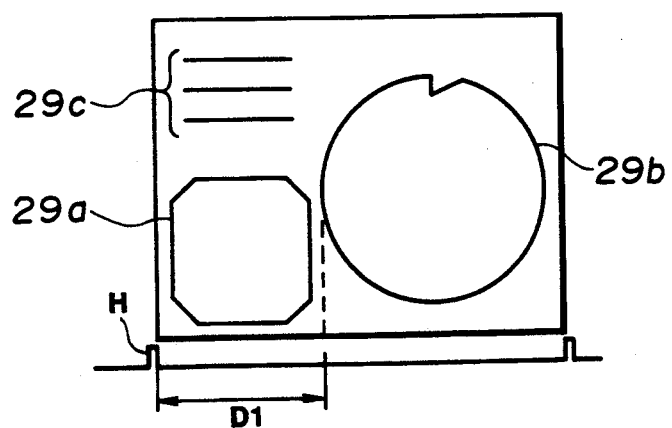

For example, when image data is to be displayed in non-reduced scale, addresses are read, as shown in FIG. 3c (forming a synchronizing signal SYNC), according to the timing that the reading is delayed by a delay HD1 relative to a horizontal synchronizing signal H. When image data is to be displayed in reduced scale, addresses are read, as shown in FIG. 3b, according to the timing that the reading is delayed by a delay HD2 relative to the horizontal synchronizing signal H. The timing for reading addresses in vertical direction also differs depending on whether image data is displayed in non-reduced or reduced scale.

Figure 5:
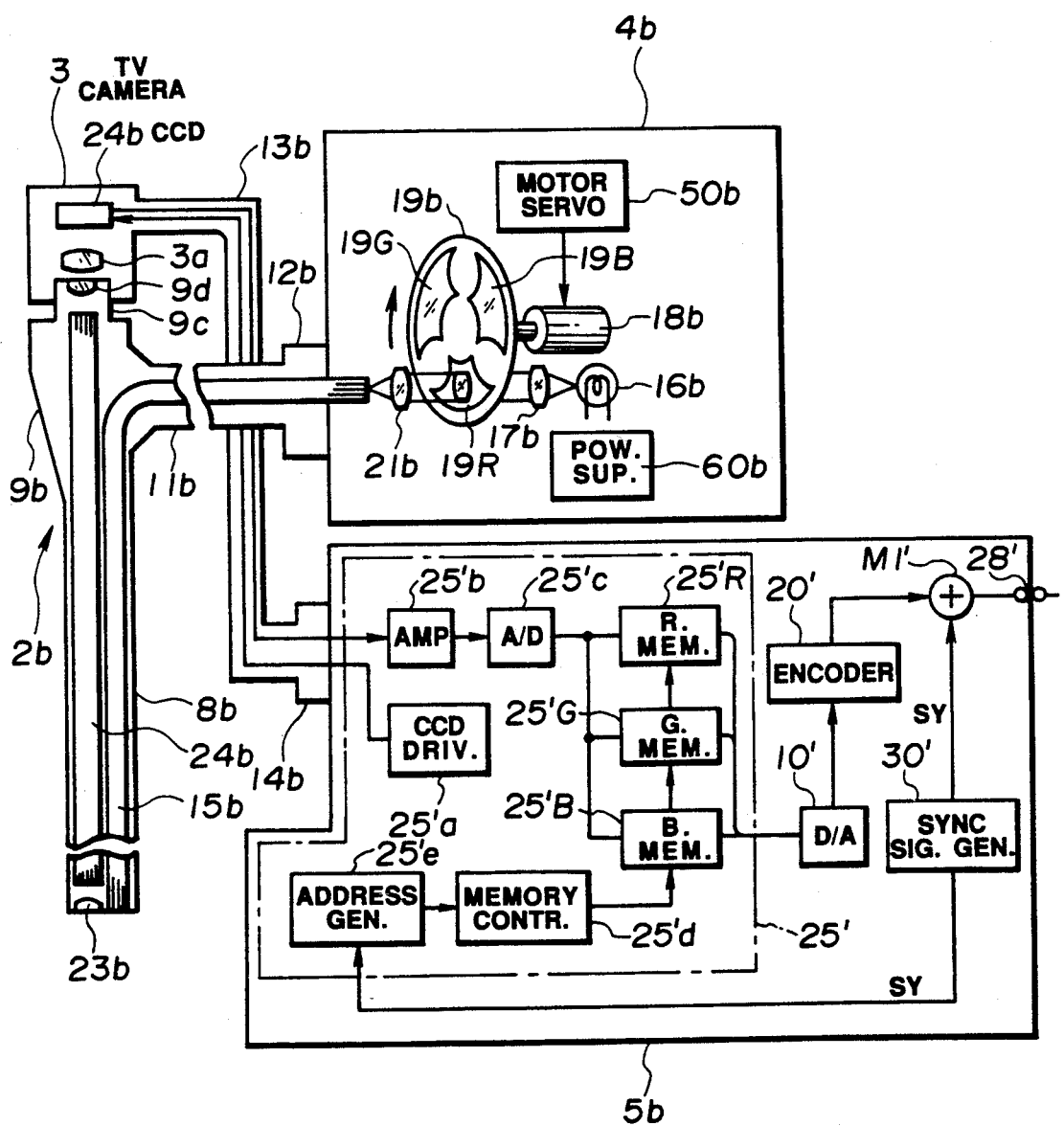

FIG. 5 shows a specific configuration of an electronic endoscope system for a child scope.

A fiberscope 2b comprises an elongated insertion tube 8b, a large-diameter operating section 9b formed at the proximal end of the insertion tube 8b, a light guide cable 11b extending from the operating section 9b, and an eyepiece section 9c formed on the top of the operation unit 9b.

A light guide 15b is running through the insertion tube 8b, operating section 9b, and light guide cable 11b. When a connector 12b formed at the end of the light guide cable 11b is connected to a light source 4b so that it will be freely detachable, illumination light is supplied from the light source 4b.

The light source 4b has the same configuration as that of the light source 4a shown in FIG. 2. Components corresponding to those shown in FIG. 2 will be assigned b instead of a. The description will be omitted.

An objective lens 23b is attached to the end (distal end) of the insertion tube 8b. One end of an image guide 24b is arranged on the focal plane of the objective lens 23b. The image guide 24b allows optical images to propagate to the other end of the image guide 24b of the end surface of the eyepiece section. An eyepiece 9d is arranged on the opposite side of the end surface of the eyepiece section. The eyepiece 9d permits enlarged observation. An image formation lens 3a is arranged in a TV camera 3 so that it will face the eyepiece 9d. The image formation lens 3a forms images transmitted through the image guide 24b on a CCD 24b.

A signal cable connected to the CCD 24b runs through a cable 13b. A connector 14b formed at the end of the cable 13b can be connected to a child scope video processor 5b.

When a drive signal originating from a CCD drive circuit 25'a in an image processing unit 25' is applied to the CCD 24b, image data is input to an amplifier 25'b in the image processing unit 25'. Then, the image data is stored sequentially in R, G, and B memories 25'R, 25'G, and 25'B under the control of a memory controller 25'd. The memory controller 25'd writes or reads image data in or from addresses given by an address generation circuit 25'e. The address generation circuit 25'e generates addresses in synchronization with a synchronizing signal SY originating from a synchronizing signal generation circuit 30'.

Image data read by the memory controller 25'd at the same time is converted into digital signals by a D/A converter 10', input to an encoder 20', then converted into, for example, NTSC video signal components. After that, the components are mixed with the synchronizing signal SY originating from the synchronizing signal generation circuit 30' to be NTSC video signal. Finally, an NTSC composite video signal is output as a standard video signal from a video signal output terminal 28'.

A keyboard 31 shown in FIG. 2 is provided with function keys 34 for sending special codes independently of character data and a trackball 35 for sending coordinate data according to the movement of the rotary ball. The special codes and coordinate data are transmitted to a CPU 33 via a keyboard interface 32.

Figure 6A:
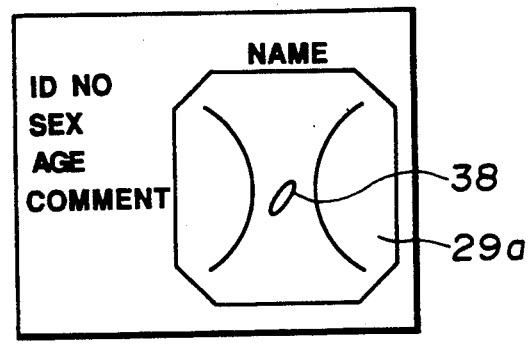
Figure 6B:
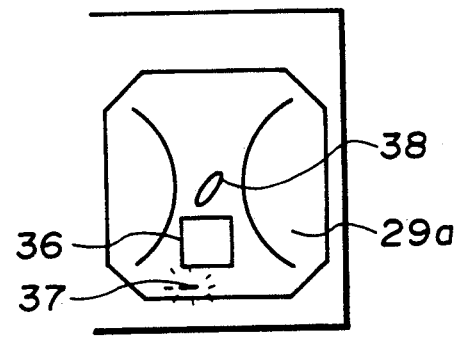
Figure 6C:
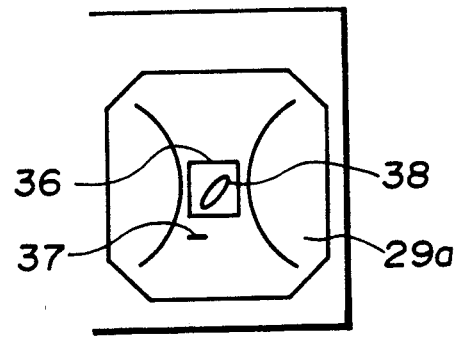
Figure 6D:
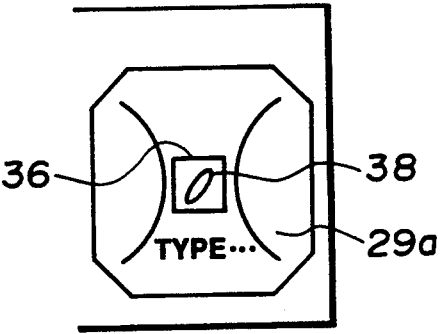

When coordinate data contained in the CPU 33 is updated, or when the trackball 35 is rolled by a user, the CPU 33 controls an image processing unit 25 so that an indication frame 36 and a cursor 37 shown in FIG. 6b will be displayed. The indication frame 36 is interlocked with the trackball 35. A user can move the indication frame 36 to enclose a lesion 38 as shown in FIG. 6c. After that, a comment, such as the one shown in FIG. 6d, can be entered at the keyboard 31.

As shown in FIGS. 7a to 7c, the size of the indication frame 36 can be changed using the function keys 34 according to the size of a lesion 38. The indication frame 36 can be enlarged or reduced by operating the function keys 34.

When a user has wanted to enclose a specific region on a recorded endoscopic image and append a comment so as to highlight a lesion 38, he/she has had to enter asterisks or other characters one-by-one to create a frame, move a cursor to an intended position for a comment, and enter a comment. However, according to the procedure shown in FIG. 6 or 7, the user can create a frame of an appropriate size using a coordinate input means; such as, a trackball. Thus, users can create comments quickly, contributing to a reduction in examination time. This eventually reduces the time of patient discomfort.

In addition, since a comment is appended to the image of a lesion, the user can easily recognize the condition of the patient. This will also be of great advantage to the patient.

According to the first embodiment, endoscopic images obtained with scopes 2a and 2b can be displayed on a single monitor 6 simultaneously. The endoscope system according to the first embodiment can be used in a limited place. In addition, it is very convenient to compare the images that two images can be displayed on the same monitor 6. According to the first embodiment, the two scopes 2a and 2b can be inserted into a body cavity. This makes it possible to observe even a complicated region in a body cavity. For example, the parent scope 2a is inserted into the esophagus, and the child scope 2b running through the channel 39 of the parent scope 2a is used to observe the small bile duct linking to the esophagus.

Figure 8:
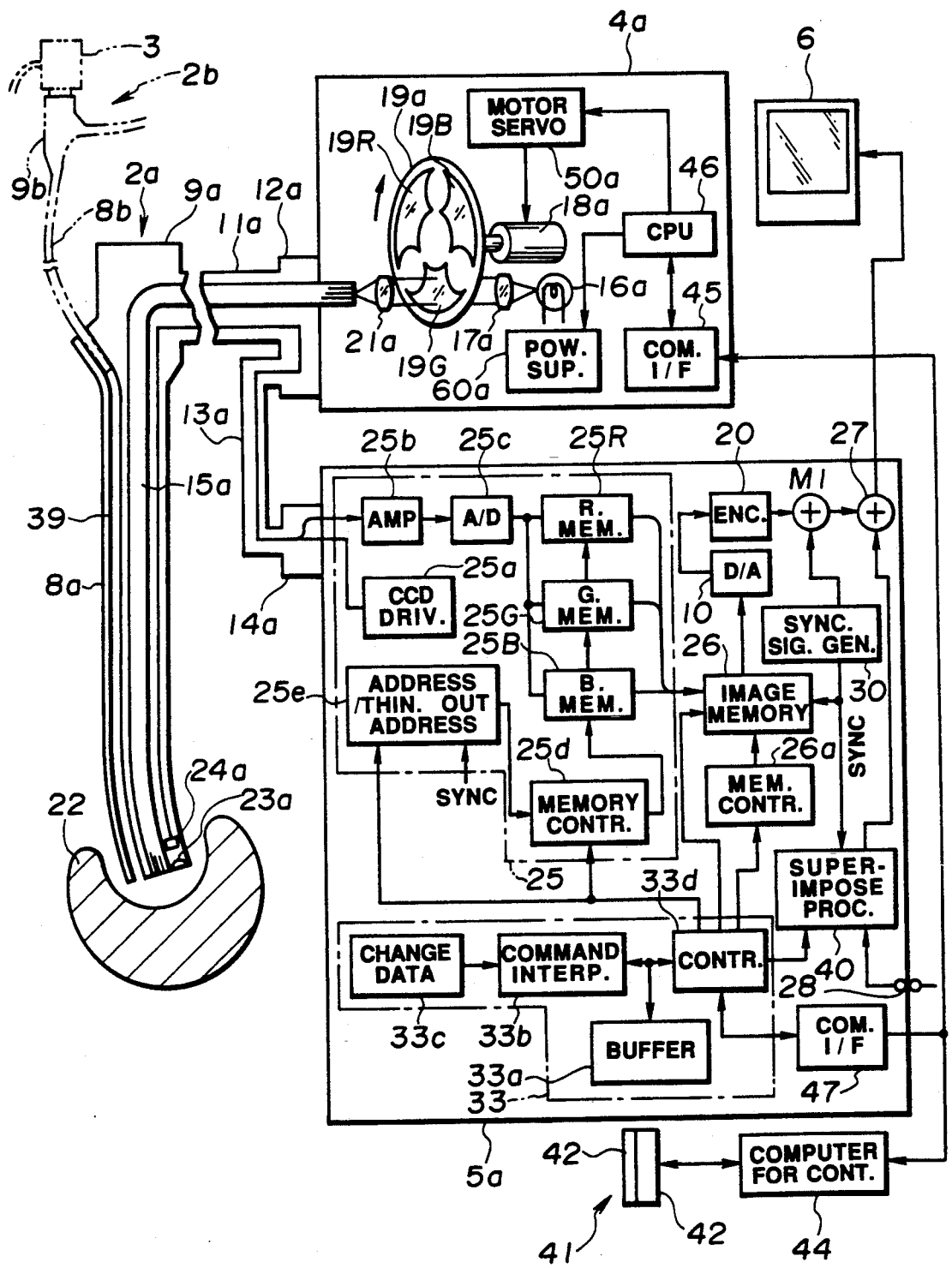
FIG. 8 is a configuration diagram showing the main section of a deformed example of the first embodiment.

FIG. 8 shows a main section of a deformed example of the first embodiment.

In this deformed example, the configuration of the endoscope system for a parent scope differs from that shown in FIG. 2. The deformed example has a centralized operation panel 41 shown in FIG. 8 instead of an operator panel, which is not shown, for use in entering set values (for example; quantity of light, color tone, AGC, and enhancement level) for the light source 4a and video processor 5a in the first embodiment. The centralized operation panel 41 also incorporates the functions of the keyboard 31 in the first embodiment.

The centralized operation panel 41 comprises liquid crystals or other display devices 42 and touch panel switches 43, wherein the display devices 42 and touch panel switches 43 are formed as a unit. Then, the centralized operation panel 41 is connected to an equipment control computer 44. The equipment control computer 44 displays an operation screen for the light source 4a or video processor 5a, or a keyboard operation screen 41A shown in FIG. 9 on the display devices 42.

If set values for equipment entered using the touch panel switches 43 are concerned with the light source 4a, the set values are sent to a CPU 46 via a communication interface 45. If the set values are concerned with the video processor 5a, they are sent to a CPU 33 (specifically, a controller 33d in the CPU 33) via a communication interface 47. This allows a user to modify the set values. In FIG. 9, switches in an indication frame operating section 48 are used to display an indication frame 36 in the same manner as that in the first embodiment. A comment can be entered using a keyboard operating section 49. Thus, this deformed example provides the same effects as the first embodiment.

A plurality of indication frames may be created as a first indication frame 51a and a second indication frame 51b shown in FIG. 10a. Furthermore, as shown in FIG. 10b, the size of an indication frame may be varied arbitrarily by moving a upper left point 52 and a lower right point 53. This will apparently improve the ease of operation.

An effect specific to this embodiment is that since the keyboard operating section corresponds to switches in software, the keys for the keyboard operating section can be re-designed uniquely for a user.

Figure 11:
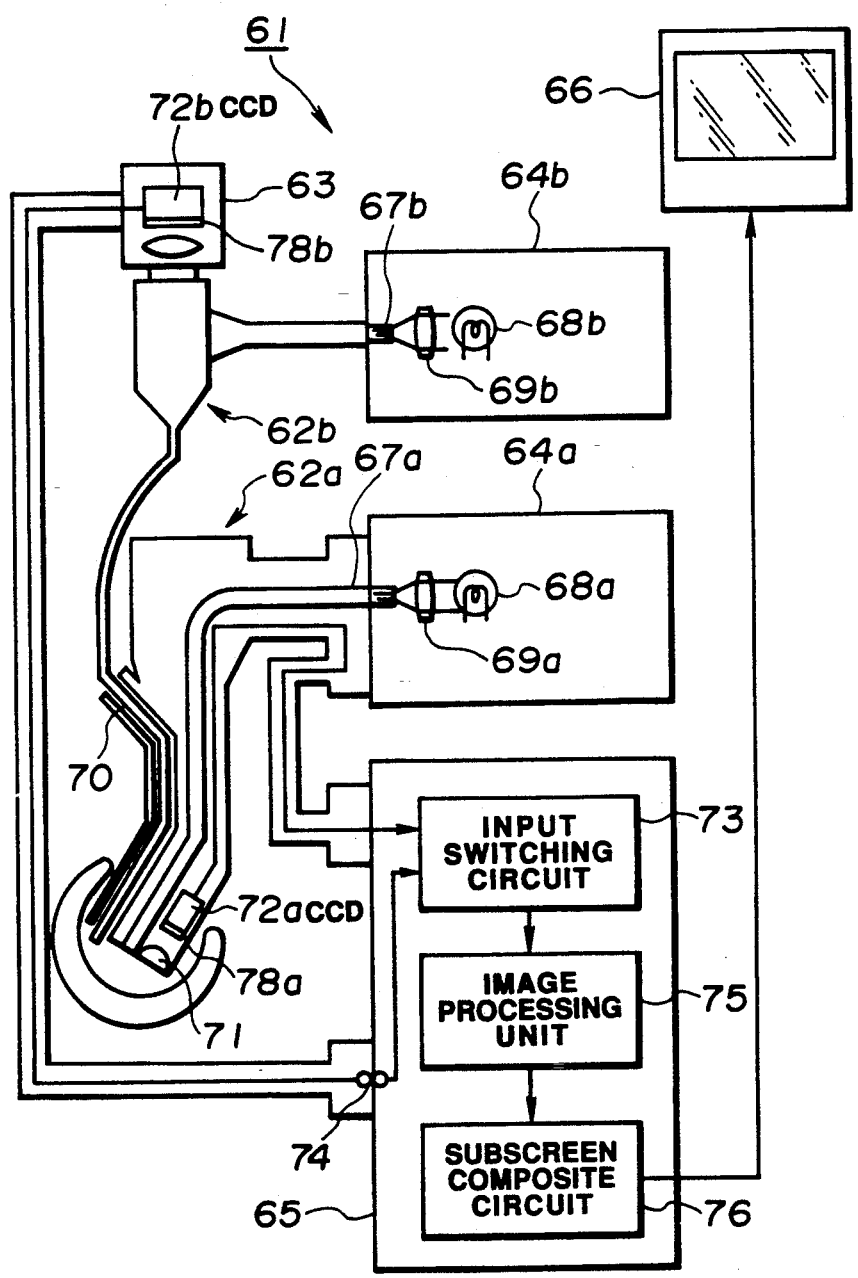
FIG. 11 is a configuration diagram of the second embodiment of the present invention.

FIG. 11 shows an electronic endoscope system 61 according to the second embodiment. The electronic endoscope system 61 comprises a parent scope 62a, a child scope 62b, a TV camera head 63 mounted on the eyepiece section of the child scope 62b, light sources 64a and 64b for supplying white illumination light to the parent scope 62a and child scope 62b, a video processor for processing signals, and a monitor 66 for displaying video signals.

Light guides 67a and 67b running through the parent scope 62a and child scope are provided with illumination light by the light sources 64a and 64b. In the light source 64a, for example, white light from a lamp 68a is converged by a lens 69a, and thus illumination light is supplied to the incident end of the light guide 67a. (Components of the light source 64b corresponding to those of the light source 64a will be assigned b instead of a. The description will be omitted.) The child scope 62 can be routed through the channel 70 of the parent scope 62.

A CCD 72 is arranged on the focal plane of an objective lens 71a at the distal end of the parent scope 62a. An image signal resulting from photoelectric transfer by the CCD 72 is input to an input switching circuit 73 in the video processor 65. A mosaic filter 78a for color separation is mounted in front of the image formation plane (photoelectric transfer plane) of the CCD 72.

In addition, a mosaic filter 78b for color separation is mounted in front of the image formation plane of the CCD 72b in the TV camera head 63 mounted on the child scope 62b.

An image signal originating from the CCD 72 is input to the input switching circuit 73 via an external input terminal 74 of the video processor 65. An output of the video processor 65 is provided to an image processing unit 75, and converted into a video signal. Then, two image signals are mixed by a subscreen composite circuit 76. As a result, two images are displayed in the same screen on the monitor 66, for example, as shown in FIG. 3b.

Figure 12:
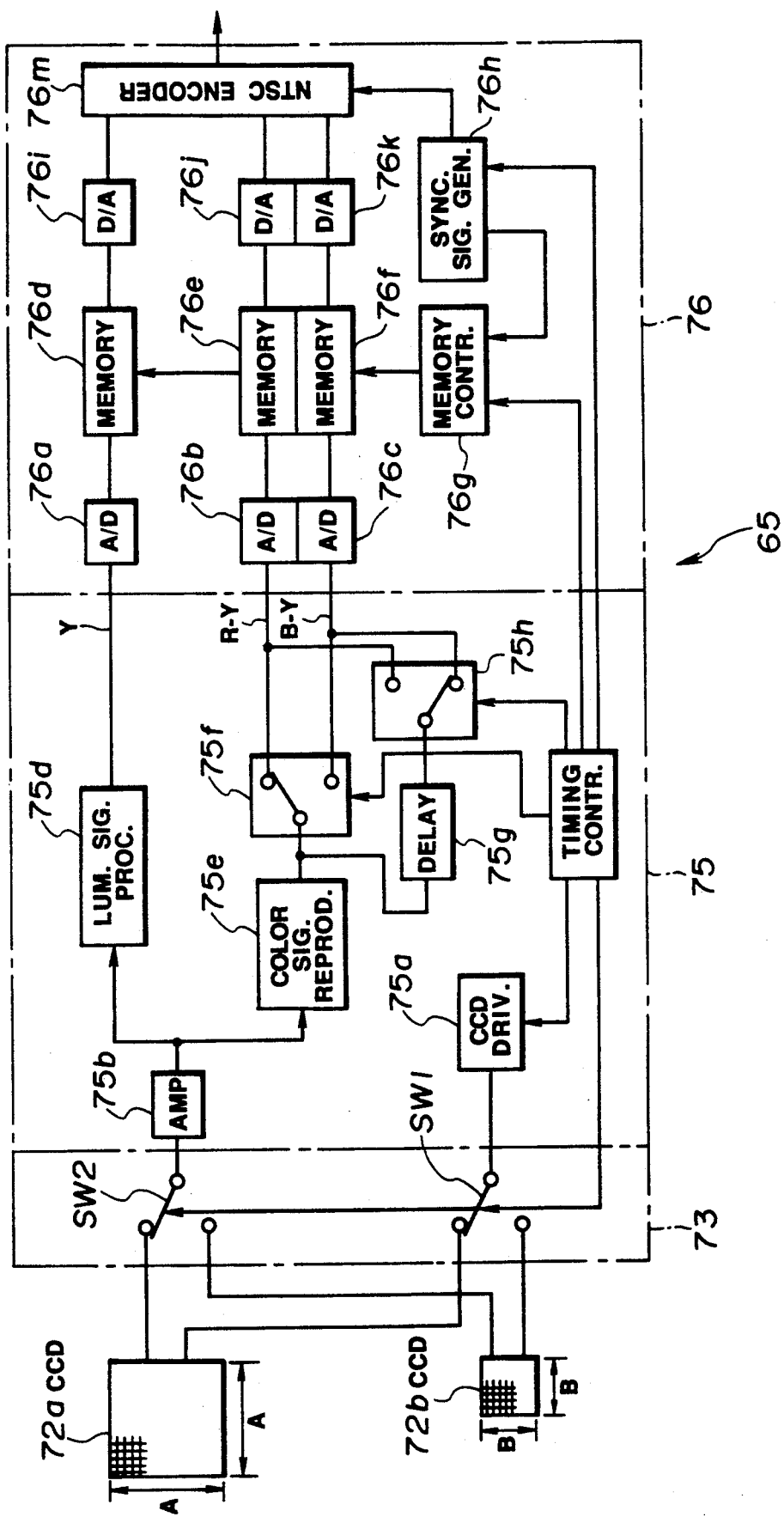
FIG. 12 is a block diagram showing the configuration of a video processor.

FIG. 12 shows a configuration of a video processor 65. A drive signal provided by a CCD driver 75a in the image processing unit 75 passes through a switch SW1 forming the input switching circuit 73, then reaches the CCD 72a or CCD 72b (whichever is connected by the SW1). The CCD 72a or CCD 72b provided with the drive signal performs photoelectric transfer and transmits a resultant signal. The signal is input to an amplifier 75b via a switch SW2, then amplified. The switch SW2 as well as the switch SW1 are interlocked, and the switches are changed over by a timing controller 75c.

A signal amplified by the amplifier 75b is input to a brightness signal processing circuit 75d and a color signal regeneration circuit 75e to generate a brightness signal Y and color difference signals $R-Y$ and $B-Y$ which are output time-sequentially for each line. The color difference signals $R-Y$ and $B-Y$ are input to a first switch 75f, a delay circuit 75g having a delay of one horizontal period, and a series circuit including a second switch 75h. An output of the second switch 75h is added to that of the first switch 75f to generate synchronized color difference signals R−Y and B−Y. The first switch 75f and second switch 75h are interlocked and changed over at intervals of half a horizontal period by the timing controller 75c.

The brightness signal Y and color difference signals R−Y and B−Y are input to A/D converters 76a, 76b, and 76c in the subscreen composite circuit 76, respectively, converted into digital signals, then temporarily written in memories 76d, 76e, and 76f. The writing timing is controlled by the timing controller 75c, and the storage areas are specified by the memory controller 76g.

In this embodiment, a drive signal is applied to the CCD 72a and CCD 72b alternately at intervals of one field period. A signal read from the CCD 72a or CDD 72b during a single field period is converted into a brightness signal Y and color difference signals R−Y and B−Y by the image processing unit 75. Then, the brightness signal Y and color difference signals R−Y and B−Y are temporarily written in different storage areas of the memories 76d, 76e, and 76f. After that, the data of two images temporality written in the memories 76d, 76e, and 76f are read out sequentially from the reading addresses by the memory controller 76g.

The read image data is input to D/A converters 76i, 76j, and 76k, converted into analog signals, then input to an NTSC encoder 76m. Then, the analog signals are converted into an NTSC composite video signal with a synchronizing signal SYNC added, then output to the monitor 66. In this embodiment, the number of pixels B generated by the CCD 72b is about half of the number of pixels A by the CCD 72a. Therefore, if analog signals are converted into a video signal as they are (without enlargement, reduction, or other processing), the video signal will be displayed as shown in FIG. 3b. When an output signal of the CCD 72a is reduced, while that of the CCD 72b is enlarged, the resultant video signal will be displayed as shown in FIG. 3c.

In this second embodiment, only one video processor 65 is needed, realizing a compact electronic endoscope system based on the parent scope 62a.

Figure 13:
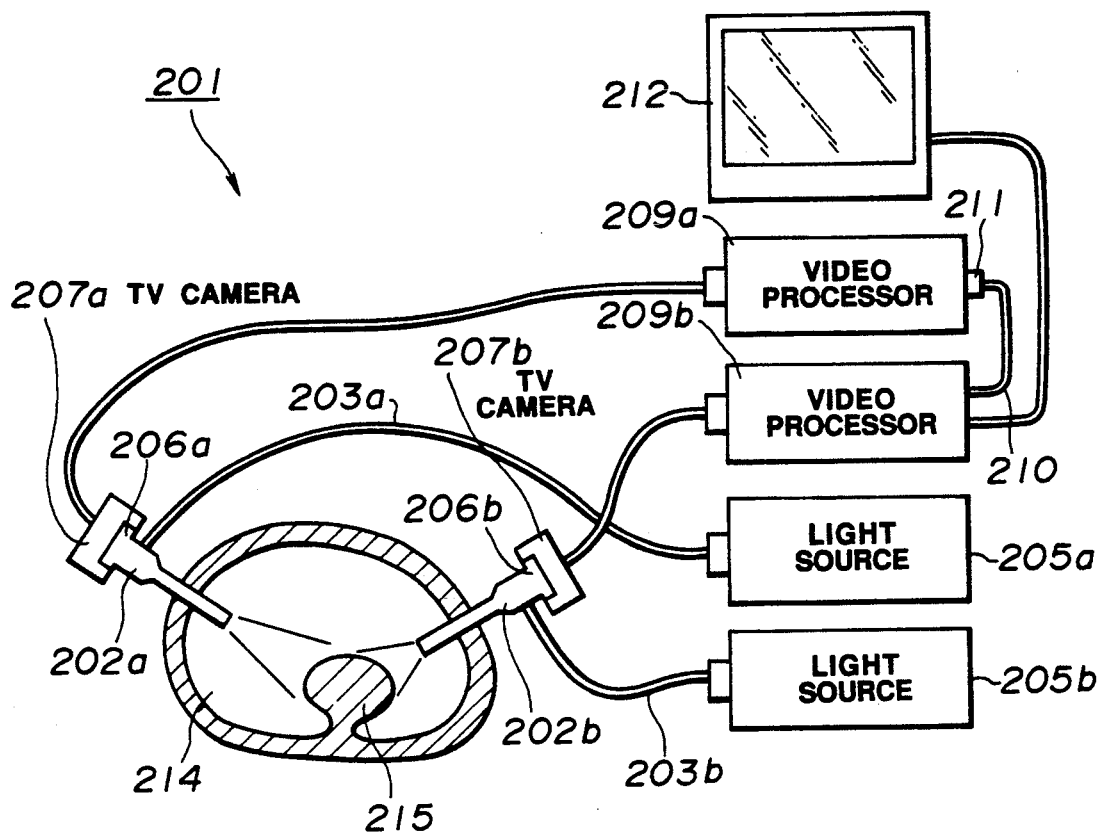
FIG. 13 is a configuration diagram of the third embodiment of the present invention.

FIG. 13 shows an endoscope video system 201 according to the third embodiment of the present invention. The system 201 is formed with two laparoscopes 202a and 202b. The laparoscopes 202a and 202b are rigid endoscopes having rigid insertion tubes for abdominal observation. Connectors 204a and 204b at the ends of light guide cables 203a and 203b extending from the laparoscopes 202a and 202b are connected to light sources 205a and 205b respectively. Thus, illumination light is supplied. The light sources 205a and 205b have the same configurations as, for example, the light sources 64a and 64b shown in FIG. 10.

TV cameras 207a and 207b are mounted on eyepiece sections 206a and 206b of the laparoscopes 202a and 202b. Cables 208a and 208b drawn out from TV cameras 207a and 207b are connected to video processors 209a and 209b, respectively. The TV cameras 207a and 207b have the same configuration as, for example, the TV camera 63 shown in FIG. 11.

A video signal which has been processed by the other video processor 209a and corresponds to an image recorded by the TV camera 207a travels along a cable 210, passes through an external video signal input terminal 211 of the other video processor 209b, then enters the video processor 209b. Then, the video signal is superimposed on a video signal corresponding to an image recorded by the TV camera 207b. Then, the resultant signal is displayed on a shared monitor 212 simultaneously.

In FIG. 13, the insertion tubes 213a and 213b of the two laparoscope 202a and 202b are inserted into an abdominal cavity 214 to observe, for example, an organ 215 contained in it.

Figure 14:
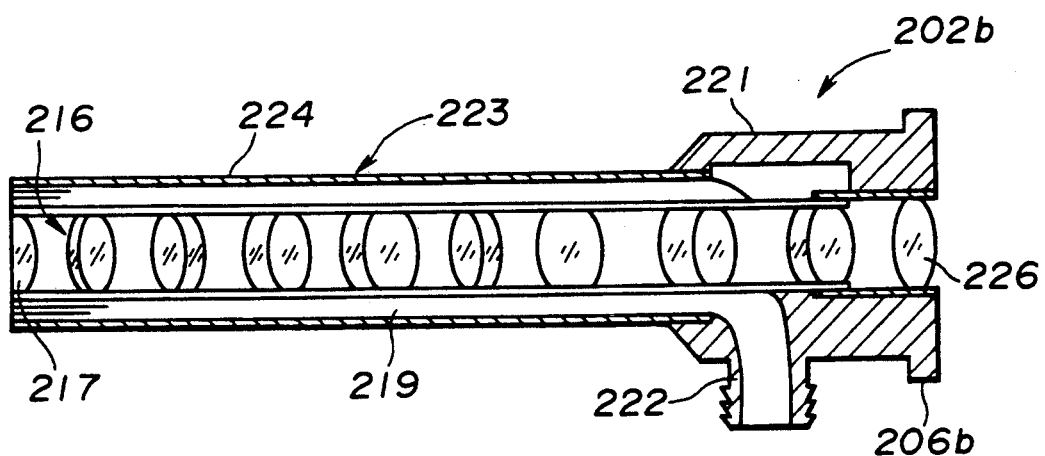
FIG. 14 is a cross-sectional diagram showing the configuration of a laparoscope.

FIG. 14 shows an example of a configuration of a rigid scope 202b. As shown in FIG. 14, in the rigid scope 202b, a relay lens system 216 is employed instead of an image guide 24b. The relay lens system 216 allows optical images formed on an objective lens 217 to propagate to an eyepiece section 206b. Thus, the optical images can be viewed through an eyepiece 226. The relay lens system 216 is locked in a lens barrel 218. A light guide 219 is running outside the lens barrel 218. The operator side of the light guide 219 is locked with a base 222 of an operating section 221. A light guide cable 203b is connected to the base 222. An insertion tube 223 of the rigid scope 202b is formed with a rigid pipe 224. Other components are identicaL to those of the fiberscope 2b.

When the two laparoscopes 202a and 202b are employed as described in this embodiment, the condition of a polyp 215 can be assessed in more detail than when one laparoscope is used.

Figure 15:
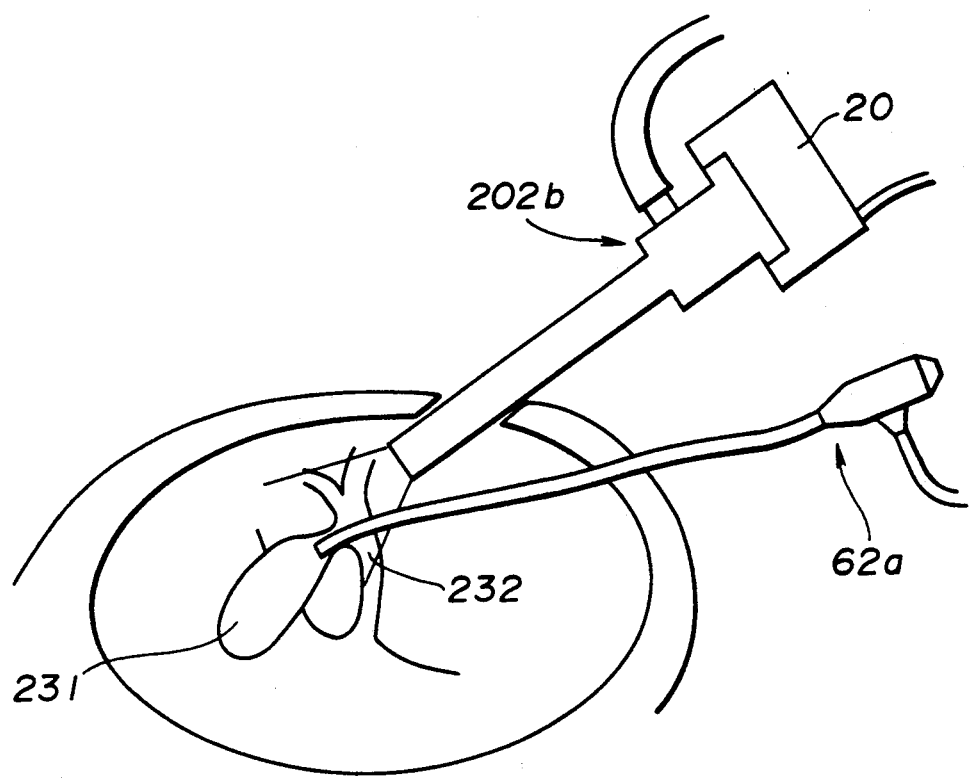
FIG. 15 is an explanatory diagram showing part of a deformed example of the third embodiment.

FIG. 15 shows part of an endoscope system according to a deformed example of the third embodiment in which an electronic endoscope 62a and a rigid scope 202b are used to observe the cholecyst 231. While the cholecyst 231 is being visualized by the rigid scope 202b inserted into a body cavity, the distal end of the electronic endoscope 62a is inserted into the cholecyst 231 to observe the internal state of the cholecyst 231. In this case, the electronic endoscope 62a must have an insertion tube with a small external diameter.

Figure 16:
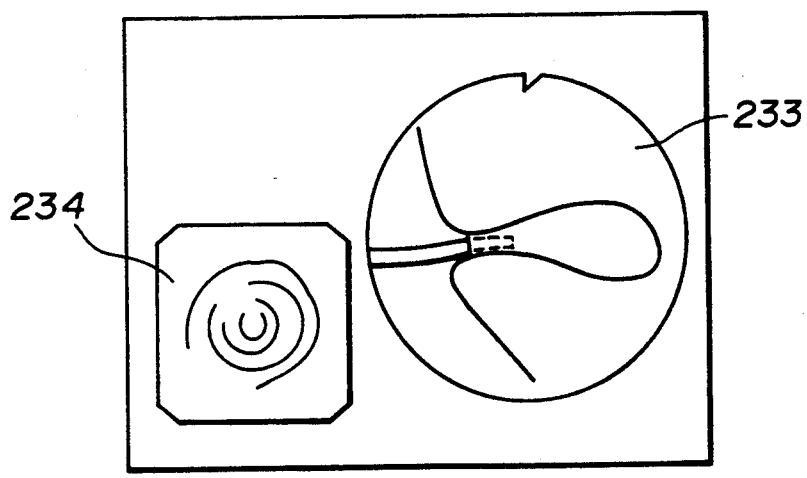
FIG. 16 is an explanatory diagram showing an image displayed on a monitor for the deformed example of the third embodiment.

In this system, an image 233 produced by the rigid scope 202b and an image 234 produced by the electronic endoscope 62a are displayed on a monitor simultaneously as shown in FIG. 16. When different types of scopes are used in combination, an object region can be assessed or treated more smoothly than when only one scope is used.

Figure 17:
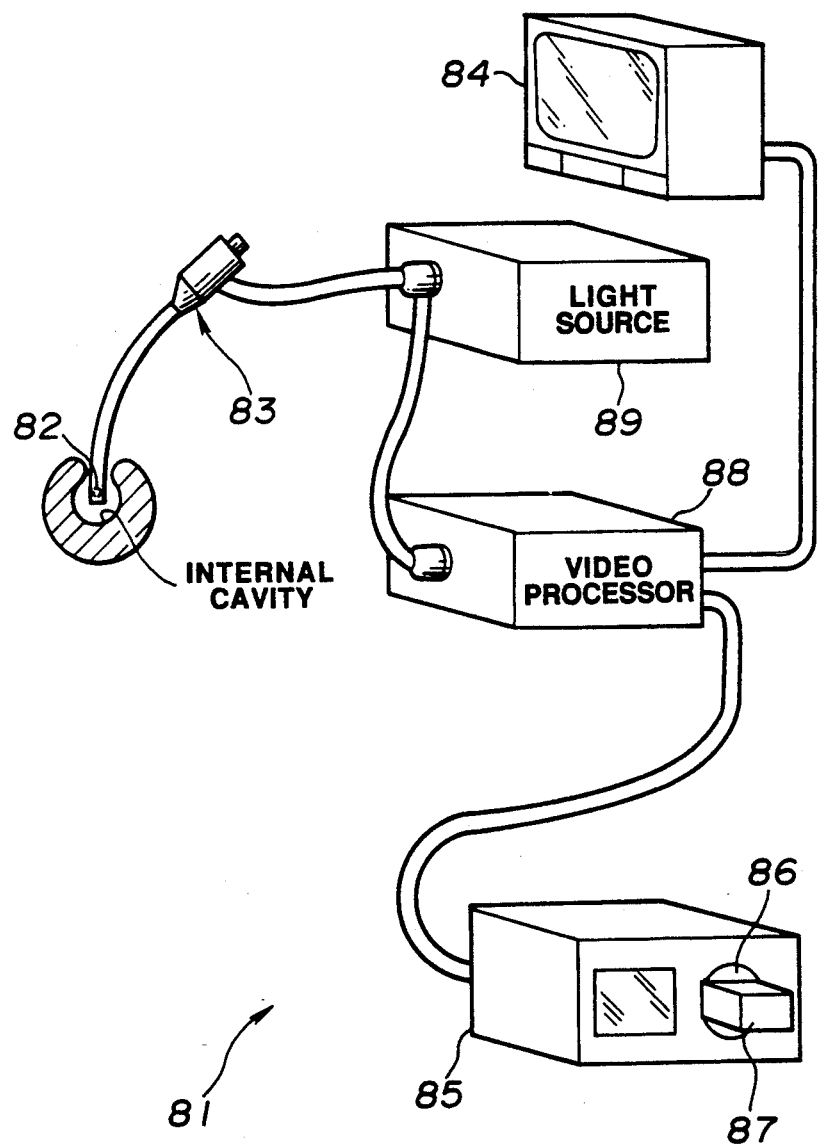
FIG. 17 is a configuration diagram of an endoscope system having a monitor image recording unit.

FIG. 17 shows an electronic endoscope system 81 including a photographic means. In FIG. 17, the endoscopic video system 81 applies a drive signal for reading a signal to a video scope 83 incorporating a CCD 82, a light source 89 or a illumination means, and the CCD 82, converts a read signal into a video signal; such as, an RGB (component) signal, and outputs the video signal to a monitor 84 and a monitor image recording unit 85. A still camera 87 is connected to the monitor image recording unit 85 via a camera adapter 86.

For photographs produced by the monitor image recording unit 85, users can change the color tone freely using a color tone adjustment means incorporated in the video processor 88.

Figure 18:
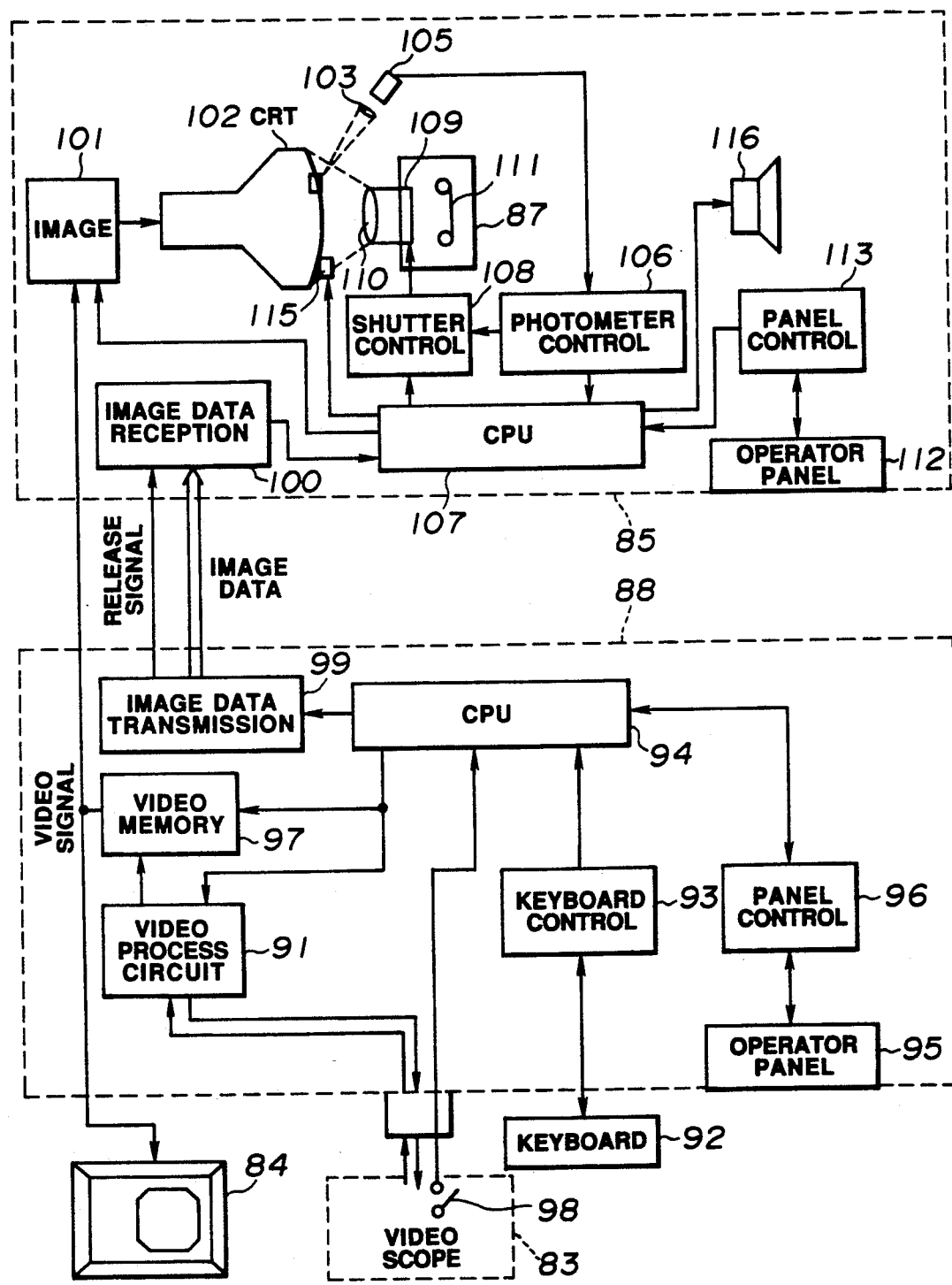
FIG. 18 is a configuration diagram of the video processor and monitor image recording unit for the system shown in FIG. 17.

FIG. 18 is a configuration diagram showing the video processor 88 and monitor image recording unit 85 of the system 81 shown in FIG. 17, and their connection.

In FIG. 18, the video processor 88 incorporates a video processing circuit 91 for applying a drive clock to the CCD 82 and converting electric signals sent from the CCD 82 into video signals.

Patient data (for example; name and sex) is entered at a keyboard 92. Input data entered by operating the keyboard 92 is input to a CPU 94 designed for setting the video processor 88 or performing operations via a keyboard control circuit 93 or an interface, then superimposed on a video signal by the video processing circuit 91.

To modify set values (for example; color tone and contour enhancement level) for the video processor 88, users must operate an operator panel 95. A set value is placed in the CPU 94 through a panel control circuit 91 or an interface with the operator panel 95. Then, the CPU 94 drives the video processing circuit 91 in the light of a modified set value. Thus, an intended endoscopic image is obtained.

A video memory 97 passes an input video signal as it is or retains it temporarily, then outputs it as a still image signal according to the contents of a control signal sent from the CPU 94. An output video signal of the video memory 97 is transmitted to the TV monitor 84 and monitor image recording unit 85. When the CPU 94 detects the fact that a release switch SW98 installed in a video scope 83 has been closed, the CPU 94 transmits a release signal to a recording data reception circuit 100 in the monitor image recording unit 85 via a recording data transmission circuit 99.

On the other hand, a color tone component of a video signal is regulated in the duration passing from the video processor 88 through a video circuit 101 in the monitor image recording unit 85, then input to a CRT 102.

Brightness of the CRT 102 is signaled to a photodiode 105 by a photometry lens 103 all the time. The photodiode 105 provides the CPU 107 with an output corresponding the received brightness (hereafter, brightness information) via a photometry control 106. In response to the release signal sent from the video processor 88, the CPU 107 actuates a shutter control circuit 108 according to the timing determined with the brightness information. Then, the shutter control 108 actuates a shutter 109.

When the shutter 109 opens, an endoscopic image of the CRT 102 is formed on film 111 via a recording lens 110. Thus, photography is performed.

In this system 81, the CPU 94 actuates the video processing circuit 91 in the light of the set values (for example, color tone and contour enhancement) for the video processor 88 a user has specified at the operator panel 95. Thus, an intended endoscopic image is obtained. At the same time, the set values for the video processor 88 (hereafter, video processor data) are transmitted from the recording data transmitter 99 to the monitor image recording unit 85.

In the monitor image recording unit 85, an exposure correction value and other set values for the monitor image recording unit 85 a user has selected at the operator panel 112 (hereafter, monitor image recording unit data) are input to the CPU 107 via the panel control circuit 113.

The CPU 107 controls the shutter control circuit 108 and video circuit 101, and inputs both the video processor data and monitor image recording unit data which have been placed in the CPU 107 via a recording data reception circuit 100 into a recording data display 115.

The recording data display 115 comprises LEDs, liquid crystals, or other display devices, which is located, for example, below the CRT 102. Monitor recording unit data designates an input signal of RGB or NTSC, an exposure control mode of AUTO or MANUAL, and an exposure correction value ranging from +1 to +3. Video processor data is a color tone set value of R+1 or B−1. The contents of display on the CRT 102 and those on the data display 115 can be reproduced on film 111 via the recording lens 110 of the still camera 87.

The photodiode 105 is used to detect the monitor brightness of the CRT 102. When the monitor brightness is too low, a buzzer 116 sounds. This helps prevent a photographic error of producing a black photograph.

According to the configuration shown in FIG. 19, monitor recording unit data is displayed on a unit located below the CRT 102. The monitor recording unit data may be displayed on the CRT 102 as shown in FIG. 20.

Figure 20:
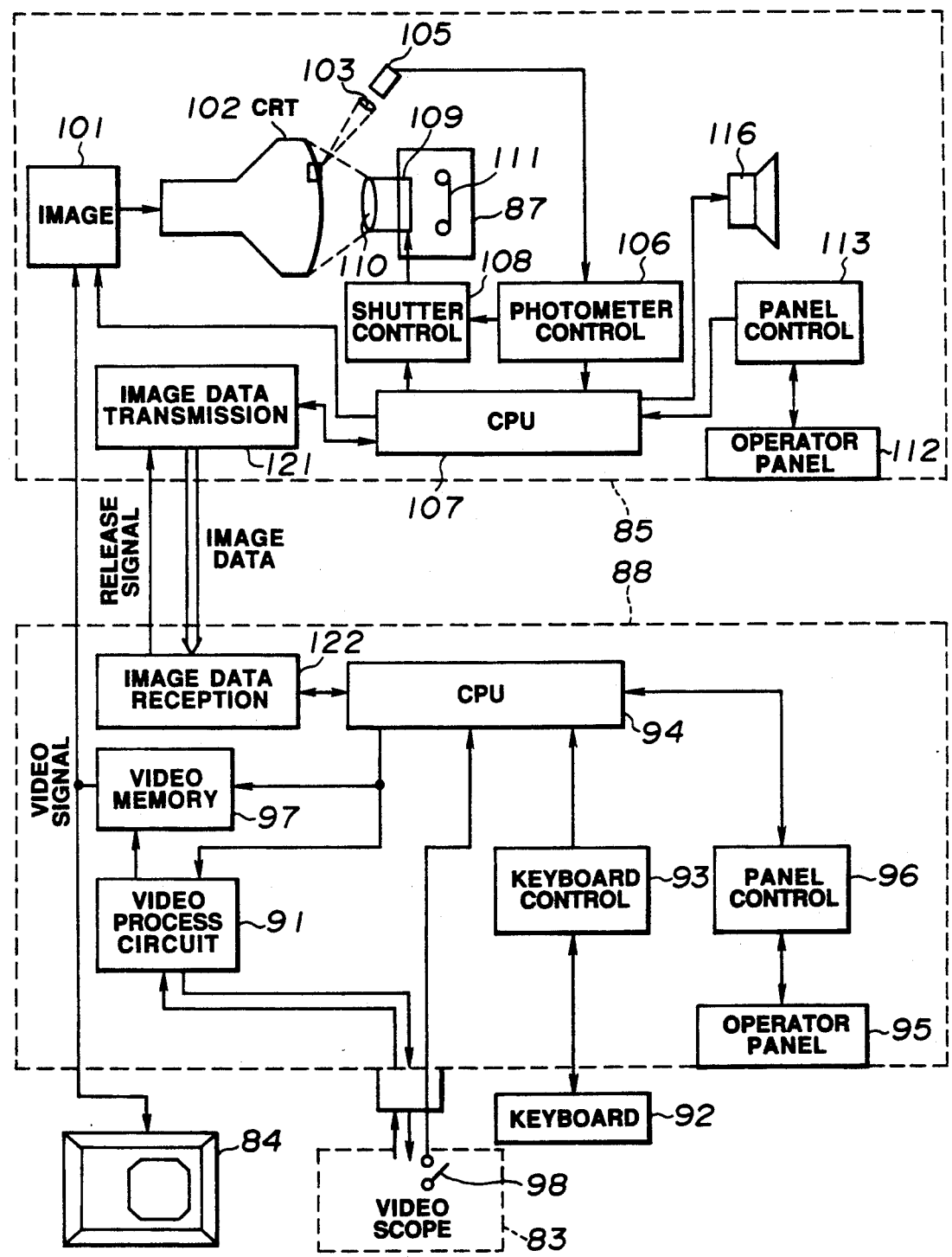
FIG. 20 is a configuration diagram showing the main section of a deformed example of the endoscope system shown in FIG. 17.

Specifically, as shown in FIG. 20, the set values for the monitor image recording unit 85 are transmitted to the video processor 88 over the recording data transmission circuit 121. Then, the video processor 88 inputs the received set values into the CPU 94 using the recording data reception circuit 122.

The CPU 94 inputs both the monitor image recording unit data and video processor data into the video processing circuit 91. In the video processing circuit, the data is superimposed to be a video signal. The video signal is output to the monitor image recording unit 85 and TV monitor 84 via the video memory 97.

Figure 19:
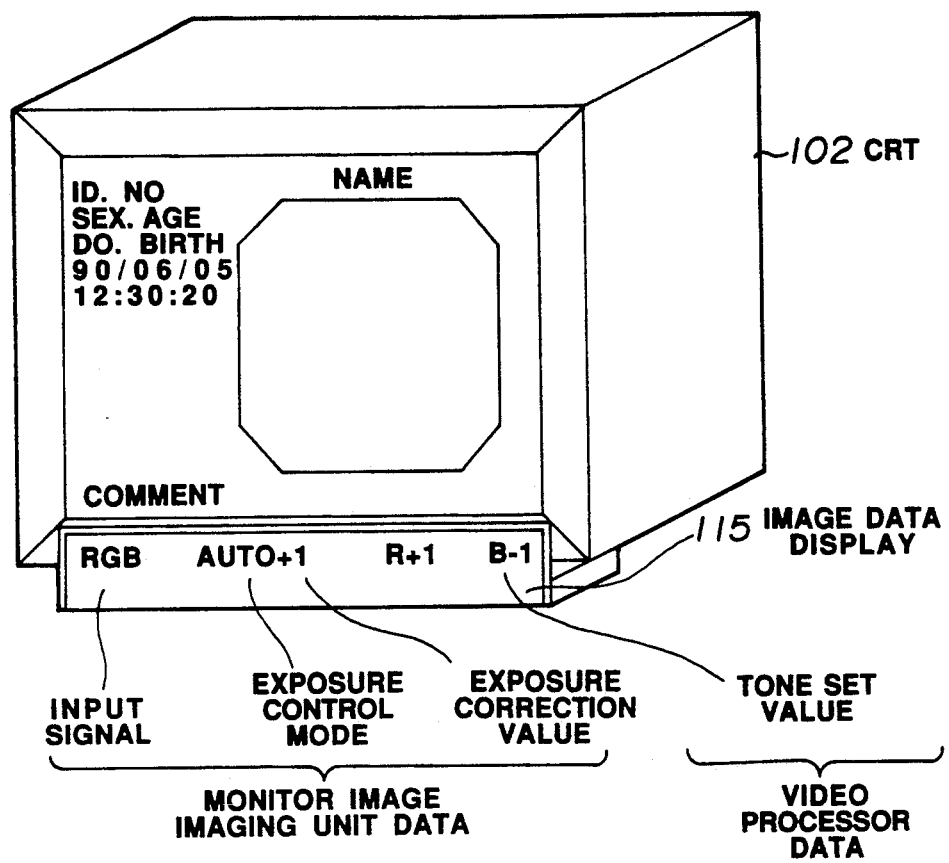
FIG. 19 is an explanatory diagram showing a CRT and the contents of a screen on a recording data display.
Figure 21:
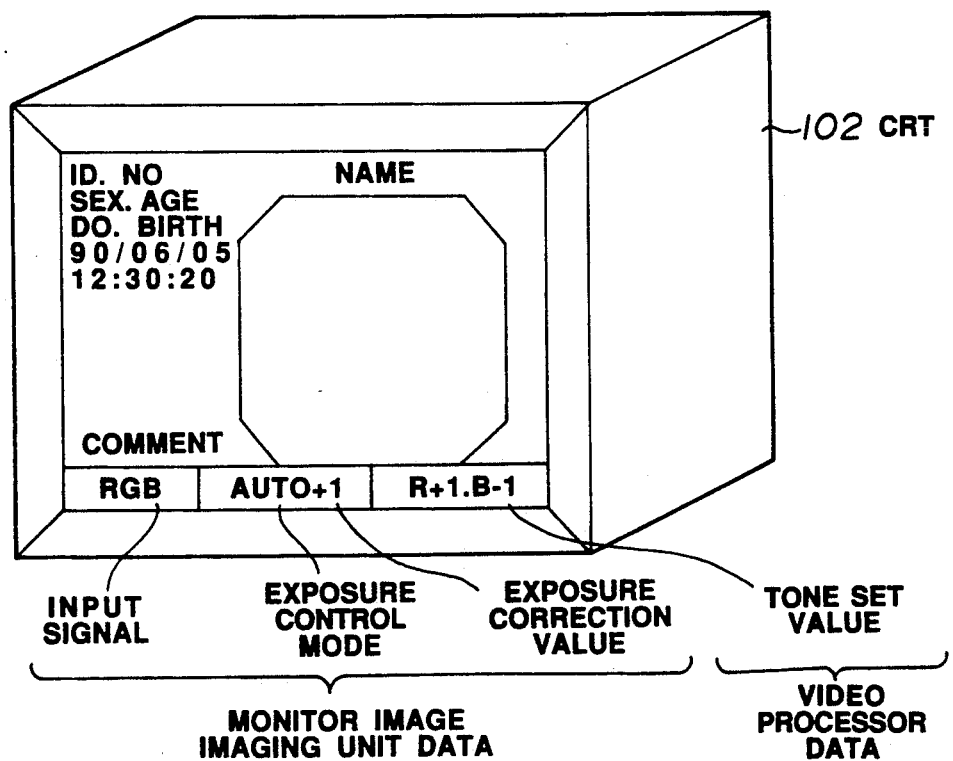
FIG. 21 is an explanatory diagram showing the contents of a screen displayed on the CRT.

Thus, in this system, the recording data display 115 shown in FIGS. 18 and 19 is not included but an area or part of the CRT 102 is assigned to the functions of the recording data display 115. Both monitor recording unit data and video processor data may be displayed in, for example, an area near a lower corner of the CRT 102. As for release operation, a release signal is transmitted from the video processor 88 to the monitor image recording unit 85 in the same way as that shown in FIG. 18. Then, the shutter 109 is actuated under the control of the CPU 107.

In this system, unlike the previous systems, data of recording conditions does not overflow the CRT 102. Therefore, images can be recorded on film 111 in a largest possible size.

In addition, even if hardware or a data display is not installed, software can be programmed to superimpose data on an endoscopic image. This helps simplify the system configuration and brings about the same effects as those realized by the previous systems.

In the aforesaid system, if the set values (for example, quantity of light and shutter speed) for the light source 89 shown in FIG. 17 are added to recording conditions, the effects of the system will be further improved.

Foregoing embodiments may be combined partly to form different embodiments which will also belong to the present invention.

What is claimed is:
1. An endoscope system, comprising:
a first endoscope including an elongated insertion tube and a first imaging means for producing a first endoscopic image;
a second endoscope including an elongated insertion tube and a second imaging means for producing a second endoscopic image;
a video processor including a function for processing a first image signal originating from said first imaging means which is input from an input terminal and a function for mixing a second image signal originating from said second imaging means which is input from an external input terminal with at least a first video signal originating from said first imag- ing means to thereby generate a composite video signal; and a monitor which is provided with said composite video signal sent from said video processor and capable of simultaneously displaying said first endoscopic image and said second endoscopic image corresponding to said composite video signal.

2. An endoscope system according to claim 1, wherein said first endoscope includes a channel through which the insertion tube of said second endoscope can be routed.

3. An endoscope system according to claim 1, wherein at least one of said first endoscope and said second endoscope is an electronic scope in which an imaging device is arranged on the focal plane of an objective optical system installed at the distal end of the insertion tube.

4. An endoscope system according to claim 1, wherein at least one of said first endoscope and said second endoscope is a fiberscope in which one end of an image guide is arranged on the focal plane of the objective optical system installed at the end of the insertion tube or a fiberscope with an external TV camera in which a TV camera incorporating an imaging device is mounted on the eyepiece section of said fiberscope.

5. An endoscope system according to claim 1, wherein said video processor processes said image signal originating from said first imaging means so that the image signal will be displayed in reduced scale on said monitor.

6. An endoscope system according to claim 1, wherein said video processor outputs an NTSC composite video signal to said monitor as said composite video signal.

7. An endoscope system according to claim 1, further comprising a monitor image recording unit for photographing images displayed on the monitor.

8. An endoscope system according to claim 1, wherein at least one of said first endoscope and said second endoscope is a rigid endoscope incorporating a relay optical system for transmitting optical images originating from an objective optical system at the distal end of the insertion tube or a rigid scope with an external TV camera in which a TV camera incorporating an imaging device is mounted on the eyepiece section of said rigid endoscope.

9. An endoscope system according to claim 8, wherein said light guides emit a plurality of illumination light beams having different wavelengths sequentially.

10. An endoscope system according to claim 1, further comprising a signal processing means for displaying said first endoscopic image and said second endoscopic image in different sizes on said monitor.

11. An endoscope system according to claim 10, wherein said signal processing means displays said first endoscopic image and said second endoscopic image by changing the sizes of the images according to data sent from an operating means.

12. An endoscope system according to claim 1, further comprising a second video processor which is connected to said second imaging means, for processing said second image signal to generate a second video signal, then outputs said second video signal to said external input terminal.

13. An endoscope system according to claim 12 wherein said second video processor processes said second image signal originating from said second imaging means so that the image signal will be displayed in reduced scale on said monitor.

14. An endoscope system according to claim 12, wherein said second video processor generates a video signal using said second image signal originating from said second imaging means and outputs the video signal in synchronization with a synchronizing signal sent from said video processor.

15. An endoscope system according to claim 1, wherein each of said first endoscope and said second endoscope has an elongated insertion tube, a light guide for transmitting illumination light is running through said insertion tube, and said light guide transmits illumination light and emits it from one end surface arranged at the end of said insertion tube.

16. An endoscope system according to claim 15, wherein the other end surfaces of said light guides are connected to light sources for emitting illumination light.

17. An endoscope system according to claim 15, wherein said light guides emit white illumination light.

18. An endoscope system according to claim 1, wherein said video processor provides includes a drive signal generation means for providing said first imaging means and said second imaging means with a drive signal in a time-sharing manner and reading said first image signal and said second image signal in a time-sharing manner.

19. An endoscope system according to claim 18, wherein said video processor includes a memory means for temporarily storing in a time-sharing manner said first image signal and said second image signal read in a time-sharing manner.

20. An endoscope system according to claim 19, wherein said video processor reads said first image signal and said second image signal from said memory means in synchronization with a synchronizing signal, then outputs the read signals to said monitor as a composite video signal mixing said first endoscopic image and said second endoscopic image.

* * * * *

UNITED STATES PATENT AND TRADEMARK OFFICE
CERTIFICATE OF CORRECTION

PATENT NO.: 5,196,928
DATED : March 23, 1993
INVENTOR(S): KARASAWA et al.

It is certified that error appears in the above-identified patent and that said Letters Patent is hereby corrected as shown below:

In the cover page, Item [75], in the Inventors' name,
change "Matsumi Oshima"
to --Mutsumi Oshima--

Signed and Sealed this

Fifteenth Day of March, 1994

Attest:

BRUCE LEHMAN

Attesting Officer

Commissioner of Patents and Trademarks